United States Patent [19]
Ponpipom et al.

[11] Patent Number: 4,554,349
[45] Date of Patent: Nov. 19, 1985

[54] ARALKYL AND ARALKENYL GLYCOSIDES AS INHIBITORS OF ANTIGEN-SPECIFIC T-CELL PROLIFERATION

[75] Inventors: Mitree M. Ponpipom, Branchburg; Tsung-Ying Shen, Westfield; Robert L. Bugianesi, Colonia, all of N.J.

[73] Assignee: Merck & Co., Inc., Rahway, N.J.

[21] Appl. No.: 540,594

[22] Filed: Oct. 11, 1983

[51] Int. Cl.[4] .............................................. C07H 5/06
[52] U.S. Cl. ...................................... 536/55; 536/4.1; 536/17.2; 536/17.5; 536/22; 536/53
[58] Field of Search ...................... 536/4.1, 17.2, 17.5, 536/22, 53, 55

[56] References Cited

U.S. PATENT DOCUMENTS 4,228,274  10/1980  Ponpipom et al. .................... 536/22

FOREIGN PATENT DOCUMENTS 0053827  6/1982  European Pat. Off. ............. 536/4.1

OTHER PUBLICATIONS

Muchmore et al., *Macrophage Regulation Immunity*, 1980, pp. 505–517.

*Primary Examiner*—Johnnie R. Brown
*Assistant Examiner*—Elli Peselev
*Attorney, Agent, or Firm*—Daniel T. Szura; Thomas E. Arther; Jesna J. Pfeiffer

[57] ABSTRACT

The invention disclosed herein relates to novel 1-deoxyglycosides, preferably 1-deoxy-D-mannopyranosides and 1-deoxy-L-rhamnopyranosides, having in the 1-position of the pyranose ring an aralkylthio/aralkenylthio, aralkyloxy/aralkenyloxy or aralkanoylamino/aralkenoylamino substituent; and to novel processes for preparing these 1-substituted-1-deoxyglycosides starting with the corresponding tetra-O-acetylglycopyranosyl bromide or amine. The 6-hydroxy group of 1-substituted-1 deoxyglycopyranosides can also be replaced by other functional groups. These aralkylthio/aralkenylthio, aralkyloxy/aralkenyloxy and aralkanoylamino/aralkenoylamino 1-deoxyglycosides are potent inhibitors of antigen-specific T-cell proliferation and are also useful as inhibitors of delayed-type hypersensitivity reactions.

9 Claims, No Drawings

ARALKYL AND ARALKENYL GLYCOSIDES AS INHIBITORS OF ANTIGEN-SPECIFIC T-CELL PROLIFERATION

BACKGROUND OF THE INVENTION

Muchmore and Blaese (in *Macrophage Regulation Immunity*, ed. by E. R. Unanue and A. S. Rosenthal, Academic Press, 1980, pp. 505–517) have suggested that certain saccharides and their derivatives are effective in part in inhibiting autologous monocyte T-cell proliferation. These workers tested the effect of various simple mono-, di- and oligosaccharides for their ability to interfere with antigen specific proliferation and found that the inhibitory activity of these substances depended on a number of factors, including the specific structure of the added saccharide, the time of addition to the cell culture and other experimental variables. The principal objective of the invention is to design and prepare aralkyl and aralkenyl glycosides which have better selectivity and enhance inhibitory potency.

DESCRIPTION OF THE INVENTION

The invention herein relates to glycopyranosides selected from mannopyranosides, 6-deoxy mannopyranosides and other 6-substituted derivatives thereof having in the one position of the pyranose ring an aralkylthio, an aralkenylthio, an aralkyloxy, an aralkenyloxy, an aralkanoylamino or an aralkenoylamino substituent which may be represented in the case of the preferred compounds by the formulas:

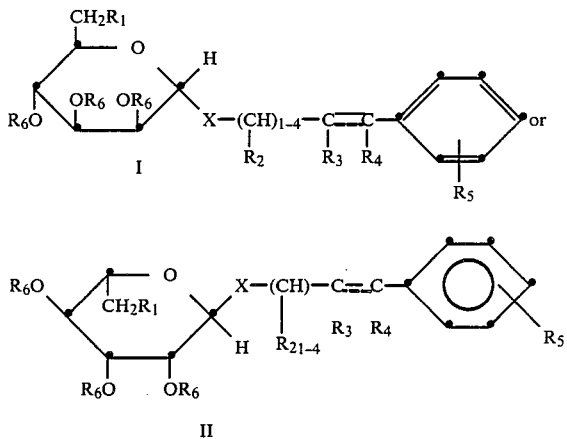

wherein the dotted line represents a carbon-carbon bond or an additional hydrogen attached to each of the carbons connected thereto;
$R_1$ is H, OH, OCH$_3$, α-D-mannopyranosyloxy, N$_3$, NH$_2$, NH-alkanoyl of 1-5 carbons, NH-oleiyl, or NH-lipoyl;
X is —S—, —O—, or

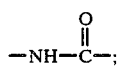

$R_2$, $R_3$ and $R_4$ are each hydrogen or lower alkyl of 1-4 carbon atoms;
$R_5$ is H, Cl, F, OH, O-alkyl of 1-4 carbons, S-alkyl of 1-4 carbons and their sulfoxide and sulfone, NRR$^1$ where R and R$^1$=H or R=H, R$^1$=alkyl of 1-4 carbons, or R=R$^1$=alkyl of 1-4 carbons; and
$R_6$ is hydrogen or lower alkanoyl of from 1-4 carbon atoms
and with novel processes for their preparation.

These novel glycopyranosides having a thio, oxy or amido linkage to an aralkyl or aralkenyl substituent are useful in the treatment of allergic reactions because of their activity as inhibitors of antigen specific T-cell proliferation and their activity as inhibitors of delayed-type hypersensitivity reactions.

The novel substituted glycosides of formulas I and II hereinabove are prepared starting with a 2-S-tetra-O-acetylglycopyranosyl-2-thiopseudourea hydrobromide or an alkali metal glycopyranosyl mercaptide in the case of the 1-position derivatives linked through a thio substituent; a tetra-O-acetylglycopyranosyl bromide in the case of the 1-position derivative linked through an oxy substituent; or a tetra-O-acetyl glycopyranosylamine in the case of 1-position derivatives linked through an NHCO substituent (X=S, O or NHCO).

The aralkyl or aralkenyl thioglycopyranosides or 6-substituted pyranosides are ordinarily prepared by reacting the corresponding 2-S-tetra-O-acetylglycopyranosyl-2-thiopseudourea hydrobromide such as 2-S-tetra-O-acetyl-α-D-mannopyranosyl-2-thiopseudourea hydrobromide or the mannopyranose sodium salt with an aralkyl or an aralkenyl bromide such as cinnamyl bromide to form the corresponding aralkyl or alkenyl thiopyranosyl compounds as for example, cinnamyl 2,3,4,6-tetra-O-acetyl-1-thio-α-D-mannopyranoside or cinnamyl 2,3,4,6-tetra-O-acetyl-1-thio-β-D-mannopyranoside. The reaction is conveniently carried out by bringing together an aqueous solution of the tetra-O acetylglycopyranosyl isothiourea. Hydrobromide and the aralkyl bromide in ethanol in the presence of potassium carbonate and potassium metabisulfite with agitation for a period of approximately 30 minutes at 25° C. The product is extracted with chloroform and the chloroform extract evaporated to dryness to obtain the product which is further purified by crystallization of the residual material from a mixture of ether and petroleum ether.

In the case of the 1-thio-β-D-mannopyranose sodium salt an aqueous ethanol mixture of the sodium salt with cinnamyl bromide is maintained at 25° C. for about 20 minutes and the reaction mixture evaporated to dryness and the residue acetylated with acetic anhydride and pyridine. The acetylated mixture is quenched in water, the solid product is separated and recrystallized from methanol.

The tetra-O-acetyl-1-thiomannopyranosides are deacetylated, if desired, by treatment with sodium methoxide in methanol for about 3 hours at 25° C. The reaction mixture is then deionized using an acidic ion exchange resin and filtered to remove the insoluble resin. The filtrate is then evaporated to dryness under reduced pressure and the residue further purified by column chromatography and/or crystallization from a lower alkanol such as isopropanol to give the desired aralkyl- or aralkenyl 1-thio-glycopyranoside including cinnamyl 1-thio-α-D-mannopyranoside, cinnamyl 1-thio-β-D-mannopyranoside, 3-phenylpropyl 1-thio-α-D-mannopyranoside, cinnamyl 2-acetamido-2-deoxy-1-thio-α-D-mannopyranoside, cinnamyl 6-O-methyl-1-thio-α-D-mannopyranoside (20), cinnamyl 6-deoxy-1-thio-α-D-mannopyranoside (22), cinnamyl 6-O-(α-D-mannopyranosyl-1-thio-α-D-mannopyranoside (24).

In the case of O-glycopyranosides the reaction is conveniently carried out by reacting the corresponding tetra-O-acetylglycopyranosyl bromide such as 2,3,4,6-tetra-O-acetyl-α-D-mannopyranosyl bromide with aralkenyl- or aralkyl alcohol such as cinnamyl alcohol to form the corresponding aralkyl or aralkenyl tetra-O-acetylglycopyranoside such as cinnamyl 2,3,4,6-tetra-O-acetyl-α-D-mannopyranoside which is deacetylated as previously described to produce the desired cinnamyl-α-D-mannopyranoside.

In the case of the 1-position derivatives of the glycopyranoside compounds linked through an amide linkage (NHCO), i.e., 1-aralkanoylamino and 1-alkenoylamino 1-deoxyglycopyranosides are readily prepared by reacting a tetra-O-acetylglycopyranosylamine such as 2,3,4,6-tetra-O-acetyl-β-D-mannopyranosylamine in the presence of a condensing agent such as dicyclohexylcarbodiimide with an aralkanoic or an aralkenoic acid such as cinnamic acid. The reaction is carried out by bringing the reactants together in solution in an organic solvent such as methylene chloride in the presence of dimethylaminopyridine at a temperature of 0.25° C. for about 1 hour with agitation. The crude reaction mixture which contains the desired product, is diluted and washed with dilute aqueous hydrochloric acid solution and aqueous sodium bicarbonate solution and the washed methylene chloride solution of product is evaporated to a small volume and subjected to column chromatography on silica gel to give the desired product cinnamoyl 2,3,4,6-tetra-O-acetyl β-D-mannopyranosylamine which is deacetylated in the manner described above to produce cinnamoyl-β-D-mannopyranosylamine.

In addition to the direct production of the compounds of our invention as described hereinabove, the compounds are also converted by hydrogenation of the aralkenyl double bond and by derivatization of the 6-position of the glycopyranosides as further set forth in the examples which follow. The specific compounds which are prepared in accordance with the attached examples are identified by name and number as follows:

(1) cinnamyl 2,3,4,6-tetra-O-acetyl-1-thio-α-D-mannopyranoside (2)
(2) cinnamyl 1-thio-α-D-mannopyranoside (3)
(3) cinnamyl 2,3,4,6-tetra-O-acetyl-1-thio-β-D-mannopyranoside (4)
(4) cinnamyl 1-thio-β-D-mannopyranoside (5)
(5) 3-Phenylpropyl 2,3,4,6-tetra-O-acetyl-1-thio-α-D-mannopyranoside (6)
(6) 3-Phenylpropyl 1-thio-α-D-mannopyranoside (7)
(7) cinnamyl 2-acetamido-3,4,6-tri-O-acetyl-2-deoxy-1-thio-α-D-mannopyranoside (8)
(8) cinnamyl 2-acetamido-2-deoxy-1-thio-α-D-mannopyranoside (9)
(9) cinnamyl 2,3,4-tri-O-acetyl-6-O-methylsulfonyl-1-thio-α-D-mannopyranoside (10)
(10) cinnamyl 2,3,4-tri-O-acetyl-6-deoxy-6-iodo-1-thio-α-D-mannopyranoside (11)
(11) cinnamyl 2,3,4-tri-O-acetyl-6-azido-6-deoxy-1-thio-α-D-mannopyranoside (12)
(12) cinnamyl 6-azido-6-deoxy-1-thio-α-D-mannopyranoside (13)
(13) cinnamyl 6-amino-6-deoxy-1-thio-α-D-mannopyranoside (14)
(14) cinnamyl 6-deoxy-6-oleamido-1-thio-α-D-mannopyranoside (17)
(15) cinnamyl 6-acetamido-6-deoxy-1-thio-α-D-mannopyranoside (15)
(16) cinnamyl 6-butyramido-6-deoxy-1-thio-α-D-mannopyranoside (16)
(17) cinnamyl 6-deoxy-6-lipoamido-thio-α-D-mannopyranoside (18)
(18) cinnamyl 2,3,4,-tri-O-acetyl-6-O-methyl-1-thio-α-D-mannopyranoside (19)
(19) cinnamyl 6-O-methyl-1-thio-α-D-mannopyranoside (20)
(20) cinnamyl 2,3,4-tri-O-acetyl-6-deoxy-1-thio-α-D-mannopyranoside (21)
(21) cinnamyl 6-deoxy-1-thio-α-D-mannopyranoside (22)
(22) cinnamyl 2,3,4-tri-O-acetyl-6-O-(tetra-O-acetyl-α-D-mannopyranosyl)-1-thio-α-D-mannopyranoside (23)
(23) cinnamyl 6-O-(α-D-mannopyranosyl)-1-thio-α-D-mannopyranoside (24)
(24) cinnamyl 1-thio-α-L-rhamnopyranoside (25)
(25) cinnamyl 1-thio-β-L-rhamnopyranoside (26)

The compounds such as described herein possess inhibitory activity against delayed-type hypersensitivity reactions in mammals. In laboratory test animals the inhibitory response is measured by using animals injected with cyclophosphamide and sheep red blood cells. After the appropriate sensitization period a challenge is administered in the foot pad with sheep red-blood cells. This challenge causes swelling of the injected foot pad in untreated animals. Previous treatment of the animals with a compound of the present invention inhibits the delayed-type hypersensitivity reaction as shown by the fact that less swelling of the injected member takes place in the treated animal. Either oral administration or i.p. injection is effective in inhibiting the delayed-type hypersensitivity reaction in the challenged test animals.

The compounds made as described herein have inhibitory activity against allergic reactions such as the delayed type hypersensitivity reactions in the range of from 5–50 mg of drug/kilogram of body weight. The actual dosage administered is based on information determined by animal test results and in addition is in part determined by the patients age, body weight and the severity of the condition being treated which, of course, depends in part on the individual patient's physical idiosyncrasies. The compounds are administered in a non-toxic dosage concentration sufficient to control the allergic condition. With these considerations in mind, the daily dosage for a particular patient can be readily determined in accordance with conventional techniques in the medical arts. Treatment is by the oral or the i.p. injection route, the preferred route being oral administration of the compound in a pharmaceutically acceptable carrier.

When the oral route of administration is used, the new compounds are compounded with a non-toxic excipient, which is edible or potable, and chemically inert to the compounds. The proportion of the excipient should be at least sufficient to separate the particles of the glycopyranoside compound from each other, and to cause quick solution or dispersion of the glycopyranoside composition when contacted with the gastric juice of the stomach. When the excipient is a solid, the amount thereof may be from about 0.3 to about 4 parts for 1 part of the active ingredient.

As solid excipients utilization may be made of lactose, sucrose, starch, pre-gelatinized starch, gum arabic, gum tragacanth and mixtures of these. Suitably, the solid excipient may contain also admixed magnesium stearate, talc, cornstarch, or two or more of these additives to promote separation of the composition from the plunger and mold used in shaping the composition into tablets for use orally.

| TABLET | |
|---|---|
| | Weight in Mgs. |
| cinnamyl 1-thio-α-D-mannopyranoside | 100.00 |
| Sucrose | 25.9 |
| Starch | 22.1 |
| Acacia | 7.8 |
| Talc | 3.1 |
| Magnesium Stearate | 1.5 |
| Stearic Acid | 1.6 |

It will be understood that the glycopyranoside derivative mentioned in the above formulation may be substituted by any of the other derivatives described and claimed herein on an equal weight basis. It is also to be considered that the glycopyranosides may be employed alone and in compatible admixtures when preparing various formulations.

In making the tablet the glycopyranoside is mixed with the sucrose and gum acacia, and then with the starch made previously into a paste with a small amount of distilled water. This mixture is dried at low heat and put through a granulator which converts it into a granular powder. This mix is then blended with the talc, magnesium stearate and the stearic acid which act as mold lubricants. The whole is now mixed in a pony mixer or other suitable powder mixing equipment, and then is ready for tableting on any type of tableting machine or for filling into hard gelatin capsules.

When the i.p. route of administration is used the intravenous preparation is simply prepared by dissolving the active compounds in distilled water in concentrations dependent upon the particular dosage unit desired.

The following examples illustrate methods of carrying out the present invention, but it is to be understood that these examples are given for purposes of illustration and not of limitation.

EXAMPLE 1A

Cinnamyl 2,3,4,6-tetra-O-acetyl-1-thio-α-D-mannopyranoside (2)

A solution of cinnamyl bromide (4.0 g, 20.3 mmol) in acetone (20 ml) is added to a solution of 2-S-(2,3,4,6-tetra-O-acetyl-α-D-mannopyranosyl)-2-thiopseudourea hydrobromide (1) (9.72 g, 20 mmol) in water (20 ml) containing potassium carbonate (3.2 g) and potassium metabisulfite (4.0 g), and the mixture is stirred vigorously for 30 minutes at room temperature. Chloroform (80 ml) and water (40 ml) are added to the mixture and the organic layer is separated and washed with water, dried, and evaporated in vacuo to dryness. The product is crystallized from ethyl ether-petroleum ether to give pure compound (9.3 g, 97%): m.p. 94°–96° C.; $[\alpha]_D^{27}+185\pm0.5°$ (C 0.98, chloroform).

Analysis calculated for $C_{23}H_{28}SO_9$: C, 57.49; H, 5.87; S, 6.67. Found: C, 57.36; H, 6.00; S, 6.95.

EXAMPLE 1B

Cinnamyl 1-thio-α-D-mannopyranoside (3)

A solution of 2 (1.0 g) in methanol (10 ml) is treated with sodium methoxide (0.05 g) for 3 hours at room temperature. It is deionized with an acidic ion-exchange resin, filtered, and the filtrate is evaporated in vacuo to a residue, which is put on a column of silica gel and eluted with $CHCl_3$—MeOH—$H_2O$ (90:10:1, v/v).

The desired fractions are combined and evaporated to a syrup which is crystallized from aqueous isopropanol to give 3 (0.54 g, 65%); m.p. 73°–75° C.; $[\alpha]_D^{27}+331\pm0.5°$ (C 1.04, methanol).

Analysis calculated for $C_{15}H_{20}SO_5$: C, 57.67; H, 6.45; S, 10.27. Found: C, 57.56; H, 6.49; S, 10.30.

EXAMPLE 2A

Cinnamyl 2,3,4,6-tetra-O-acetyl-1-thio-β-D-mannopyranoside (4)

A solution of cinnamyl bromide (0.45 g) in ethanol (4 ml) is added to a solution of 1-thio-β-D-mannopyranose sodium salt (0.5 g) in water (6 ml). After 20 minutes at room temperature, the solution is evaporated in vacuo to a crystalline mass. Pyridine (10 ml) and acetic anhydride (10 ml) are added, and the solution is kept at room temperature for 3 hours and poured into ice-water. The solid is collected and washed with cold water. Recrystallization from methanol affords 4 (0.93 g, 85%); m.p. 113°–114° C.; $[\alpha]_D^{27}-130\pm1.0°$ (C 1.0, chloroform).

Analysis calculated for $C_{23}H_{28}SO_9$: C, 57.49; H, 5.87; S, 6.67. Found: C, 57.67; H, 5.78; S, 6.71.

EXAMPLE 2B

Cinnamyl 1-thio-β-D-mannopyranoside (5)

A solution of 4 (500 mg) in dry methanol (10 ml) is deacetylated with sodium methoxide (25 mg), and worked up in the normal manner to give a crystalline mass. Recrystallization from isopropanol affords 5 in near quantitative yield (323 mg); m.p. 145°–146° C.; $[\alpha]_D^{27}-215\pm1.0°$ (C 0.97, methanol).

Analysis calculated for $C_{15}H_{20}SO_5$: C, 57.67; H, 6.45; S, 10.26. Found: C, 57.43; H, 6.51; S, 10.25.

EXAMPLE 3A

3-Phenylpropyl 2,3,4,6-tetra-O-acetyl-1-thio-α-D-mannopyranoside (6)

A solution of 2 (800 mg) in ethyl acetate (10 ml) and acetic acid (10 μl) containing 10% palladium-on-charcoal (400 mg) is hydrogenated overnight at room temperature. The catalyst is filtered off and washed with ethyl acetate. The combined filtrates are evaporated in vacuo to give 6 (780 mg, 97%); m.p. 73°–74° C. (ethyl ether-petroleum ether); $[\alpha]_D^{27}+86.0\pm0.9°$ (C 1.08, chloroform).

Analysis calculated for $C_{23}H_{30}SO_9$: C, 57.24; H, 6.27; S, 6.65. Found: C, 56.94; H, 6.29; S, 6.95.

EXAMPLE 3B

3-Phenylpropyl 1-thio-α-D-mannopyranoside (7)

Compound 6 (500 mg) is deacetylated with sodium methoxide in methanol to give 7 (300 mg, 92%): m.p. 122°–123° C. ($H_2O$); $[\alpha]_D^{27}+185.4\pm0.9°$ (C, 1.06, methanol).

Analysis calculated for $C_{15}H_{22}SO_5$: C, 57.30; H, 7.05; S, 10.20. Found: C, 57.29; H, 7.13; S, 10.05.

EXAMPLE 4A

Cinnamyl 2-acetamido-3,4,6-tri-O-acetyl-2-deoxy-1-thio-α-D-mannopyranoside (8)

Boron trifluoride etherate (200 μl, 1.3 mmol) is added to a solution of 2-acetamido-1,3,4,6-tetra-O-acetyl-2- deoxy-α-D-mannopyranose (389 mg) and cinnamyl mercaptan (150 mg) in chloroform (10 ml), and the solution is kept under nitrogen for 2 days. Another portion of boron trifluoride etherate (200 μl) is added and the solution is kept under nitrogen for another 2 days. Chloroform (15 ml) is added and the solution is washed with aqueous sodium hydrogencarbonate and water, dried, and evaporated in vacuo to a residue, which is purified by preparative chromatography (EtOAc—CHCl$_3$, 10:90, v/v, as a developing phase) to give the title compound (250 mg, 52%).

Analysis calculated for $C_{23}H_{29}NSO_8 \cdot 0.7H_2O$: C, 56.13; H, 6.23; N, 2.85; S, 6.52; Found: C, 55.96; H, 6.16; N, 2.71; S, 6.69.

EXAMPLE 4B

Cinnamyl 2-acetamido-2-deoxy-1-thio-α-D-mannopyranoside (9)

Compound 8 (120 mg) is deacetylated with sodium methoxide in methanol to give 9 (80 mg); m.p. 156°–157° C. (MeOH—EtOAc).

EXAMPLE 5A

Cinnamyl 2,3,4-tri-O-acetyl-6-O-methylsulfonyl-1-thio-α-D-mannopyranoside (10)

The title compound is prepared from 2-S-(2,3,4-tri-O-acetyl-6-O-methylsulfonyl-α-D-mannopyranosyl)-2-thiopseudourea and cinnamyl bromide in the usual manner. The desired product is isolated by column chromatography (silica gel; CHCl$_3$—EtOAc, 92:8, v/v) in 65–70% yield: m.p. 111°–113° C. (ether-petroleum ether); $[α]_D^{27} + 175 \pm 1.1°$ (C 1.0, chloroform).

EXAMPLE 5B

Cinnamyl 2,3,4-tri-O-acetyl-6-deoxy-6-iodo-1-thio-α-D-mannopyranoside (11)

A suspension of 10 (2.0 g) and sodium iodide (1.0 g) in DMF (15 ml) is heated with stirring for 16 hours at 70° C. (bath temperature). The mixture is evaporated in vacuo to a residue, which is partitioned between chloroform and water. The organic layer is dried and evaporated to a syrup (2.0 g), which is put on a column of silica gel and eluted with CHCl$_3$—EtOAc (95:5, v/v). The title compound is isolated in 94% yield: m.p. 91°–92° C. (MeOH); $[α]_D^{27} + 203 \pm 0.9°$ (C 1.06, CHCl$_3$).

Analysis calculated for $C_{21}H_{25}ISO_7$: C, 45.99; H, 4.60; S, 5.85; Found: C, 45.85; H, 4.62; S, 6.09.

EXAMPLE 5C

Cinnamyl 2,3,4-tri-O-acetyl-6-azido-6-deoxy-1-thio-α-D-mannopyranoside (12)

A suspension of 11 (8.0 g) and sodium azide (2.0 g) in DMF (100 ml) is heated with stirring for 24 hours at 85° C. (bath temperature). The solvent is evaporated in vacuo and the residue is partitioned between chloroform and water. The organic layer is separated and washed with water, dried, and evaporated to a thick syrup (7.2 g, 98%): $[α]_D^{27} + 107 \pm 0.5°$ (C 1.0, chloroform).

Analysis calculated for $C_{21}H_{25}N_3SO_7$: C, 54.41; H, 5.41; N, 9.07, S, 6.92; Found: C, 54.75; H, 5.60; N, 9.08, S, 7.10.

EXAMPLE 5D

Cinnamyl 6-azido-6-deoxy-1-thio-α-D-mannopyranoside (13)

A solution of 12 (4.4 g) in dry methanol (60 ml) is deacetylated with sodium methoxide (0.5 g). The product is isolated in the normal manner and purified by column chromatography (CHCl$_3$—MeOH—H$_2$O, 95:5:5, v/v) to give 13 as an oil (2.5 g, 78%): $[α]_D^{27} + 220 \pm 0.9°$ (C 1.06 methanol).

Analysis calculated for $C_{15}H_{19}N_3SO_4$: C, 53.40; H, 5.68; N, 12.45, S, 9.51; Found: C, 53.26; H, 5.79; N, 12.31, S, 9.57.

EXAMPLE 5E

Cinnamyl 6-amino-6-deoxy-1-thio-α-D-mannopyranoside (14)

Hydrogen sulfide is bubbled for 1 hour into a solution of 13 (1.6 g) in chloroform (15 ml) containing triethylamine (1 ml). The flask is sealed and kept for 18 hours at room temperature. The solution is evaporated in vacuo and the residue is put on a column of silica gel and eluted with CHCl$_3$—MeOH—NH$_4$OH (70:30:3, v/v). The title compound is isolated in 68% yield (1.0 g): m.p. 166°–167° C. (MeOH—Et$_2$O); $[α]_D^{27} + 385 \pm 1.0°$ (C 0.97, MeOH).

Analysis calculated for $C_{15}H_{21}NSO_4$: C, 57.85; H, 6.80; N, 4.50; S, 10.30; Found: C, 57.52; H, 6.94; N, 4.39; S, 10.37.

EXAMPLE 5F

Cinnamyl 6-deoxy-6-oleamido-1-thio-α-D-mannopyranoside (17) and cinnamyl 6-acetamido-6-deoxy-1-thio-α-D-mannopyranoside (15)

A solution of 14 (200 mg) and oleic anhydride (1 ml) in methanol (10 ml) is kept overnight at room temperature. The mixture is evaporated in vacuo and partitioned between chloroform and water. The organic layer is separated and washed with 10% sodium carbonate and water, dried, and evaporated to a syrup (two spots), which is put on a column of silica gel and eluted with chloroform-methanol-water (95:5:0.5, v/v). The more mobile compound (contaminated with oleic acid) is repurified to give the 6-deoxy-6-oleamido derivative 17 (70 mg, 19%), MS:m/e 575 (M+), 458 (M+—CH$_2$Ch=CH—C$_6$H$_5$), 426 (M+—SCH$_2$—CH=CHC$_6$H$_5$).

The other product is identified as the 6-acetamido-6-deoxy analog 15 (130 mg, 57%): m.p. 183°–185° C.; $[α]_D^{27} + 338 + 2.3°$ (C 1.09, methanol); MS:m/e 353 (M+), 236 (M+—CH$_2$CH=CHC$_6$H$_5$), 204 (M+—SCH$_2$CH=CHC$_6$H$_5$).

Analysis calculated for $C_{17}H_{23}NSO_5$: C, 57.77; H, 6.56; N, 3.96; S, 9.07; Found: C, 57.66; H, 6.71; N, 3.60; S, 8.88.

EXAMPLE 5G

Cinnamyl 6-butyramido-6-deoxy-1-thio-α-D-mannopyranoside (16)

A solution of 14 (200 mg) and butyric anhydride (1.0 g) in methanol (10 ml) is kept overnight at room temperature, and evaporated in vacuo to a residue which is partitioned between chloroform and water. The organic layer is separated and washed with 10% sodium carbonate and water, dried, and evaporated to a crystalline mass. Recrystallization from methanol-ethyl acetate affords pure material (120 mg, 48%); m.p. 165°–166° C.; $[\alpha]_D + 338 \pm 0.9°$ (C 1.1, methanol).

Analysis calculated for $C_{19}H_{27}NSO_5$: C, 59.82; H, 7.14; N, 3.67; S, 8.41; Found: C, 59.69; H, 7.27; N, 3.63; S, 8.21.

EXAMPLE 5H

Cinnamyl 6-deoxy-6-lipoamido-1-thio-α-D-mannopyranoside (18)

A solution of 14 (70 mg) and N-(lipoyloxy)succinmide* (75 mg) in tetrahydrofuran (5 ml) containing triethylamine (50 μl) is kept overnight at room temperature. The solution is evaporated in vacuo to a residue (100 mg), which is purified by column chromatography ($CHCl_3$—MeOH—$H_2O$, 95:5:0.5, v/v) to give the title compound (34 mg); m.p. 189°–190° C. (MeOH); $[\alpha]_D^{27} + 143°$ (C 1.0, DMF).

*N-(Lipoyloxy)succinimide. N-Hydroxysuccinimide (1.15 g, 10 mmol) is added to a solution of lipoic acid (2.06 g, 10 mmol) and DCC (2.1 g, 10.2 mmol) in tetrahydrofuran (10 ml). The reaction mixture is stirred for 65 hours at room temperature, filtered, and the filtrate is evaporated in vacuo to a crystalline mass. Crystallization from toluene affords the title compound (1.8 g, 59%), m.p. 85°–87° C.

Analysis calculated for $C_{23}H_{33}NS_3O_5$: C, 55.28; H, 6.66; N, 2.80; S, 19.25; Found: C, 55.29; H, 6.85; N, 2.75; S, 14.44.

EXAMPLE 6A 1,2,3,4-Tetra-O-acetyl-6-O-methyl-β-D-mannopyranose

A solution of 1,2,3,4-tetra-O-acetyl-β-D-mannopyranose (2.94 g) in dichloromethane (30 ml) at 0° C. is reacted with excess diazomethane in dichloromethane containing boron trifluoride etherate (0.12 ml). After 2 hours, the reaction mixture is filtered and excess diazomethane is destroyed with glacial acetic acid. The filtrate is washed successively with aqueous sodium hydrogencarbonate and water, dried, and evaporated in vacuo to a syrup (3.0 g). A portion of the product is crystallized from ethanol, m.p. 102°–103°, $[\alpha]_D^{27} - 16.0 \pm 1.0°$ (C 1.02, chloroform).

Analysis calculated for $C_{15}H_{22}O_{10}$: C, 49.72; H, 6.12; Found: C, 49.69; H, 6.42.

EXAMPLE 6B

Cinnamyl 2,3,4-tri-O-acetyl-6-O-methyl-1-thio-α-D-mannopyranoside (19)

A solution of 1,2,3,4-tetra-O-acetyl-6-O-methyl-β-D-mannopyranose (2.8 g) in dry dichloromethane (2 ml) at 0°–5° C. is treated with 30% hydrobromic acid in glacial acetic acid (25 ml) for 2 hours. The reaction mixture is worked-up in the normal manner to give 2,3,4-tri-O-acetyl-6-O-methyl-α-D-mannopyranosyl bromide (2.8 g), which is reacted with thiourea (0.76 g) in dry acetone (5 ml) at reflux temperature for 2 hours. The solution is evaporated in vacuo to a syrup, which is partitioned between ethyl ether (25 ml) and water (25 ml). The aqueous layer is extracted three times with ethyl ether. A solution of cinnamyl bromide (1.44 g) in acetone (30 ml) is added to the aqueous solution containing 2-S-(2,3,4-tri-O-acetyl-6-O-methyl-α-D-mannopyranosyl)-2-thiopseudourea hydrobromide. This is followed by the addition of potassium carbonate (1.26 g) and potassium metabisulfite (1.77 g) and the reaction mixture is stirred vigorously for 2 hours at room temperature. Acetone is evaporated in vacuo and the product is extracted with chloroform and washed twice with water. The solution is dried and evaporated to an oil, which is put on a column of silica gel and eluted with $CHCl_3$—EtOAc (98:2, v/v). The desired fractions are combined and evaporated in vacuo to give 19 as an oil (1.15 g, 33% overall yield): $[\alpha]_D^{27} + 147°$ (C 2.08, chloroform).

Analysis calculated for $C_{22}H_{28}SO_8 \cdot H_2O$: C, 56.16; H, 6.43; S, 6.81; Found: C, 56.18; H, 5.93; S, 7.06.

EXAMPLE 6C

Cinnamyl 6-O-methyl-1-thio-α-D-mannopyranoside (20)

Compound 19 is deacetylated with sodium methoxide in methanol and purified by preparative TLC with $CHCl_3$—MeOH (9:1, v/v) as an irrigant to give an oil, $[\alpha]_D^{27} + 287°$ (C 1.17, methanol).

Analysis calculated for $C_{16}H_{22}SO_5 \cdot H_2O$: C, 55.80; H, 7.02; S, 9.31; Found: C, 56.00; H, 6.59; S, 9.60.

EXAMPLE 7A

Cinnamyl 2,3,4-tri-O-acetyl-6-deoxy-1-thio-α-D-mannopyranoside (21)

1,2,3,4-Tetra-O-acetyl-6-deoxy-D-mannose (5 mmol) is treated with 30% HBr in HOAc to give 2,3,4-tri-O-acetyl-6-deoxy-α-D-mannopyranosyl bromide, which is dissolved in acetone (10 ml) and reacted with thiourea (0.3 g) for 1 hour at reflux temperature. The reaction mixture is processed in the normal manner to give the corresponding thiouronium salt. To a stirred solution of this salt in water (10 ml) is added cinnamyl bromide (1.0 g) in acetone (10 ml), potassium carbonate (0.6 g) and potassium metabisulfite (0.7 g). The reaction mixture is stirred vigorously for 1 hour and evaporated in vacuo to a residue, which is partitioned between chloroform and water. The organic layer is dried and evaporated to a syrup, which is put on a column of silica gel and eluted with $CHCl_3$—EtOAc (99:1, v/v). The title compound is isolated in 46% yield (0.98 g), MS: m/e 422. (M.+), 362 (M.+—HOAc), 302 (M.+—2HOAc), 273 (M.+—$SCH_2CH=CHC_6H_5$).

EXAMPLE 7B

Cinnamyl 6-deoxy-1-thio-α-D-mannopyranoside (22)

Compound 21 is deacetylated with sodium methoxide in methanol to give 22 in near quantitative yield: $[\alpha]_D^{27} + 354°$ (C 1.0, chloroform); MS:m/e 296 (M.+), 278 (M.+—$H_2O$), 147 (M.+—$SCH_2CH=CHC_6H_5$).

Analysis calculated for $C_{15}H_{20}SO_4 \cdot 0.5H_2O$: C, 58.99; H, 6.93; S, 10.50; Found: C, 59.32; H, 6.78; S, 10.71.

EXAMPLE 8A

Cinnamyl 2,3,4-tri-O-acetyl-6-O-(tetra-O-acetyl-α-D-mannopyranosyl)-1-thio-α-D-mannopyranoside (23)

A solution of 1,2,3,4-tetra-O-acetyl-6-O-(tetra-O-acetyl-α-D-mannopyranosyl)-β-D-mannopyranose (1.7 g) in 33% hydrogen bromide in glacial acetic acid (10 ml) is kept at 0°–5° C. for 1.5 hours. The reaction mixture is worked up in the normal manner to give 2,3,4-tri-O-acetyl-6-O-(tetra-O-acetyl-α-D-mannopyranosyl)-α-D-mannopyranosyl bromide (1.8 g), which is dissolved in dry acetone (5 ml) and reacted with thiourea (0.3 g) at reflux temperature for 6 hours. The solution is evaporated in vacuo to a residue, which is partitioned between ethyl ether and water. The thiouronium salt in the aqueous layer is reacted directly with a solution of cinnamyl bromide (0.54 g) in acetone (30 ml) in the presence of potassium carbonate (0.47 g) and potassium bisulfite (0.66 g) for 2 hours at room temperature. The reaction mixture is processed in the normal manner to give a syrup (1.7 g), which is put on a column of silica gel and eluted with CHCl$_3$—EtOAc (9:1, v/v). The desired fractions are combined and evaporated to give 23 (0.91 g, 47% overall yield): $[\alpha]_D^{27}+150\pm0.9°$ (C 1.14, chloroform).

Analysis calculated for $C_{35}H_{44}SO_{17}$: C, 54.68; H, 5.77; S, 4.17; Found: C, 54.36; H, 5.90; S, 4.30.

EXAMPLE 8B

Cinnamyl 6-O-(α-D-mannopyranosyl)-1-thio-α-D-mannopyranoside (24)

Compound 23 is deacetylated with sodium methoxide in methanol to give 24, $[\alpha]_D^{27}+272\pm1.0°$ (C 1.03, methanol).

Analysis calculated for $C_{21}H_{31}SO_{10}$: C, 53.04; H, 6.57; S, 6.74; Found: C, 52.49; H, 6.47; S, 6.78.

EXAMPLE 9

Cinnamyl 1-thio-α-L-rhamnopyranoside (25) and Cinnamyl 1-thio-β-L-rhamnopyranoside (26)

2,3,4-Tri-O-acetyl-α-L-rhamnopyranosyl bromide (prepared from 32 g of 1,2,3,4-tetra-O-acetyl-L-rhamnopyranose and 32% hydrogen bromide in glacial acetic acid) is reacted with potassium ethylxanthate (14 g) in dry acetone (125 ml) at reflux temperature for 5 minutes. After cooling, the mixture is poured into ice-cold water. Next day, the resulting syrup is separated by decantation and dried in high vacuo (30 g, a mixture of anomers; α:β, 43:57 as estimated by NMR). NMR (CDCl$_3$) δ6.12 (d, $J_{1,2}=1.5$ Hz, H-1α), 5.70 (d, $J_{1,2}=1.0$ Hz, H-1β), 5.63 (q, $J_{2,3}=3.0$ Hz, H-2β), 5.47 (q, $J_{2,3}=3.0$ Hz, H-2α), 3.92 (m, H-5α), 3.70 (m, H-5β).

A suspension of this crude syrup (17 g) in methanol (100 ml) is cooled to −10° C. and treated, under stirring and cooling with a solution of sodium methoxide (3 g) in methanol (20 ml). The starting material goes into solution as deacetylation taken place. After 90 minutes, ethanol (300 ml) and ethyl ether (1 l) are added and the flocculent precipitate is filtered to give 1-thio-rhamnopyranose sodium salt (6.5 g, 75%) as a mixture of anomers; α:β, 43:57 as estimated by NMR.

Cinnamyl bromide (3.0 g, 15.2 mmol) is added to the above mixture (3.0 g, 14.8 mmol) in water-ethanol (1:1, 30 ml), and the mixture is stirred for 1 hour at 50° C. and concentrated to dryness. The residue is put on a column of silica gel and eluted with CHCl$_3$—MeOH—H$_2$O (90:10:1, v/v). The more mobile component is identified as the α-anomer 25 (700 mg): $[\alpha]_D^{27}-347°$ (C 1.0, chloroform); NMR (CDCl$_3$) δ 5.23 (b, H-1), 1.34 (d, J=6.5 Hz, CH$_3$).

Analysis calculated for $C_{15}H_{20}SO_4$: C, 60.78; H, 6.80; S, 10.82; Found: C, 61.20; H, 6.96; S, 10.76.

The β-anomer 26 crystallizes upon isolation. Recrystallization from methylene chloride-ethyl ether affords pure material (500 mg): m.p. 121°-124° C.; $[\alpha]_D^{27}+176.2°$ (C 1.0, chloroform); NMR (CDCl$_3$) δ 4.62 (b, H-1), 1.38 (d, J=6.5 Hz, CH$_3$).

Analysis calculated for $C_{15}H_{20}SO_4.0.5H_2O$: C, 58.99; H, 6.93; S, 10.50; Found: C, 58.57; H, 6.80; S, 10.35.

What is claimed is:

1. Glycosides of the formulas:

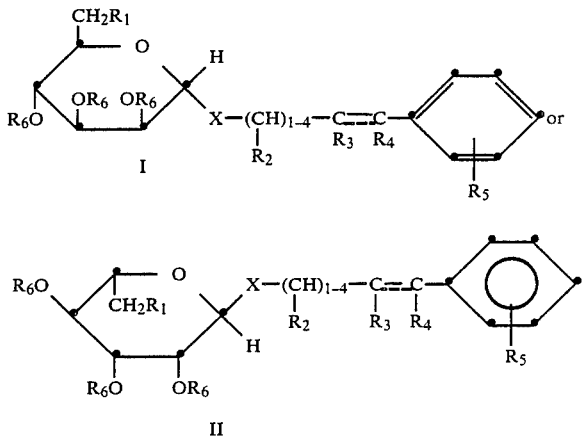

wherein the dotted line represents a carbon-carbon bond or an additional hydrogen attached to each of the carbons connected thereto;

R$_1$ is H, OH, OCH$_3$, α-D-mannopyranosyloxy, N$_3$, NH$_2$, NH-alkanoyl of 1–5 carbons, NH-oleiyl, or NH-lipoyl;

X is —S—, —O—, or

R$_2$, R$_3$ and R$_4$ are each hydrogen or lower alkyl of 1–4 carbon atoms;

R$_5$ is H, Cl, F, OH, O-alkyl of 1–4 carbons, S-alkyl of 1–4 carbons and their sulfoxide and sulfone, NRR$^1$ where R and R$^1$=H, or R=H, R$^1$=alkyl of 1–4 carbons, or R=R$^1$=alkyl of 1–4 carbons; and R$_6$ is hydrogen or lower alkanoyl of from 1–4 carbon atoms.

2. A glycopyranosyl compound of claim 1 wherein the glycopyranose moiety is selected from the group consisting of α-D-mannose, β-D-mannose, α-L-mannose, β-L-mannose, α-D-rhamnose, β-D-rhamnose, α-L-rhamnose or β-L-rhamnose.

3. A glycopyranosyl compound according to claim 1 wherein the per-O-acetyl glycopyranose moiety is selected from the group consisting of α-D-mannose, β-D-mannose, α-L-rhamnose or β-L-rhamnose.

4. A glycopyranosyl compound according to claim 2 wherein the glycopyranose moiety is α-D-mannose.

5. A compound according to claim 4 which is selected from the group consisting of
cinnamyl 2,3,4,6-tetra-O-acetyl-1-thio-α-D-mannopyranoside (2)
cinnamyl 1-thio-α-D-mannopyranoside (3)
3-Phenylpropyl 2,3,4,6-tetra-O-acetyl-1-thio-α-D-mannopyranoside (6)
3-Phenylpropyl 1-thio-α-D-mannopyranoside (7)
cinnamyl 2-acetamido-3,4,6-tri-O-acetyl-2-deoxy-1-thio-α-D-mannopyranoside (8)
cinnamyl 2-acetamido-2-deoxy-1-thio-α-D-mannopyranoside (9)
cinnamyl 2,3,4-tri-O-acetyl-6-O-methylsulfonyl-1-thio-α-D-mannopyranoside (10)
cinnamyl 2,3,4-tri-O-acetyl-6-deoxy-6-iodo-1-thio-α-D-mannopyranoside (11)

cinnamyl 2,3,4-tri-O-acetyl-6-azido-6-deoxy-1-thio-α-D-mannopyranoside (12)
cinnamyl 6-azido-6-deoxy-1-thio-α-D-mannopyranoside (13)
cinnamyl 6-amino-6-deoxy-1-thio-α-D-mannopyranoside (14)
cinnamyl 6-acetamido-6-deoxy-1-thio-α-D-mannopyranoside (15)
cinnamyl 6-butyramido-6-deoxy-1-thio-α-D-mannopyranoside (16)
cinnamyl 6-deoxy-6-oleamido-1-thio-α-D-mannopyranoside (17)
cinnamyl 6-deoxy-6-lipoamido-thio-α-D-mannopyranoside (18)
cinnamyl 2,3,4,-tri-O-acetyl-6-O-methyl-1-thio-α-D-mannopyranoside (19)
cinnamyl 6-O-methyl-1-thio-α-D-mannopyranoside (20)
cinnamyl 2,3,4-tri-O-acetyl-6-deoxy-1-thio-α-D-mannopyranoside (21)
cinnamyl 6-deoxy-1-thio-α-mannopyranoside (22)
cinnamyl 2,3,4-tri-O-acetyl-6-O-(tetra-O-acetyl-α-D-mannopyranosyl)-1-thio-α-D-mannopyranoside (23)
cinnamyl 6-O-(α-D-mannopyranosyl)-1-thio-α-D-mannopyranoside (24).

6. A compound according to claim 2 wherein the glycopyranose moiety is β-D-mannose.

7. A compound according to claim 6 which is selected from the group consisting of
cinnamyl 2,3,4,6-tetra-O-acetyl-1-thio-β-D-mannopyranoside (4) and
cinnamyl 1-thio-β-D-mannopyranoside (5).

8. A compound according to claim 3 wherein the glycopyranose moiety is α-L-rhamnose.

9. A compound according to claim 8 which is selected from the group consisting of
cinnamyl 1-thio-α-L-rhamnopyranoside (25) and
cinnamyl 1-thio-β-L-rhamnopyranoside (26).

* * * * *